US007396683B2

(12) United States Patent
Bolbot et al.

(10) Patent No.: US 7,396,683 B2
(45) Date of Patent: Jul. 8, 2008

(54) DETECTION OF ALLERGEN-ASSOCIATED MATERIALS

(75) Inventors: John Anthony Bolbot, Cranfield (GB); Steven John Setford, Bedford (GB); Stephen Frederick White, Kempston (GB)

(73) Assignee: Cranfield University, Bedfordshire (GB)

( * ) Notice: Subject to any disclaimer, the term of this patent is extended or adjusted under 35 U.S.C. 154(b) by 362 days.

(21) Appl. No.: 10/416,341

(22) PCT Filed: Nov. 12, 2001

(86) PCT No.: PCT/GB01/05001

§ 371 (c)(1),
(2), (4) Date: Oct. 20, 2003

(87) PCT Pub. No.: WO02/39115

PCT Pub. Date: May 16, 2002

(65) Prior Publication Data

US 2004/0058454 A1    Mar. 25, 2004

(30) Foreign Application Priority Data

Nov. 10, 2000    (GB)    ................................ 0027487.8

(51) Int. Cl.
*G01N 27/00* (2006.01)
*G01N 27/26* (2006.01)
(52) U.S. Cl. .................. 436/149; 436/151; 204/400; 204/403.01; 205/775

(58) Field of Classification Search ................. 436/149, 436/150, 151, 177; 422/82.01, 82.02; 204/400, 204/403.01, 403.02; 205/775
See application file for complete search history.

(56) References Cited

U.S. PATENT DOCUMENTS

| 5,476,797 A | * | 12/1995 | Matsunaga ................... 436/513 |
| 5,679,535 A | | 10/1997 | Joyce et al. |
| 5,723,345 A | * | 3/1998 | Yamauchi et al. ............ 436/518 |
| 5,958,791 A | | 9/1999 | Roberts et al. |
| 6,130,097 A | * | 10/2000 | Polzius et al. ................ 436/169 |
| 6,375,896 B1 | * | 4/2002 | Wuske et al. ................... 422/58 |
| 6,387,614 B1 | * | 5/2002 | Cheng et al. ..................... 435/4 |
| 6,551,495 B1 | * | 4/2003 | Porter et al. ............... 205/777.5 |

FOREIGN PATENT DOCUMENTS

| EP | 0 423 801 | 4/1991 |
| JP | 63 317096 | 12/1988 |
| JP | 02 159554 | 6/1990 |
| JP | 6-288976 | 10/1994 |
| JP | 2001 153838 | 6/2001 |
| WO | WO 91/10900 | 7/1991 |

* cited by examiner

*Primary Examiner*—Jan M. Ludlow
(74) *Attorney, Agent, or Firm*—Oblon, Spivak, McClelland, Maier & Neustadt, P.C.

(57) ABSTRACT

Measurement of the redox properties of household dust is used to detect the presence of allergen-associated materials. Measurement may be electrochemical, preferably amperometric. A disposable electrode assembly may be made by screen printing with conductive (e.g. carbon and Ag/AgCl) inks. An absorbent pad overlying the electrodes can be used to wipe a surface to collect a sample. It may contain electrolyte and buffer components, so that adding water carries sample in an electrolyte/buffer solution to the electrodes.

23 Claims, 2 Drawing Sheets

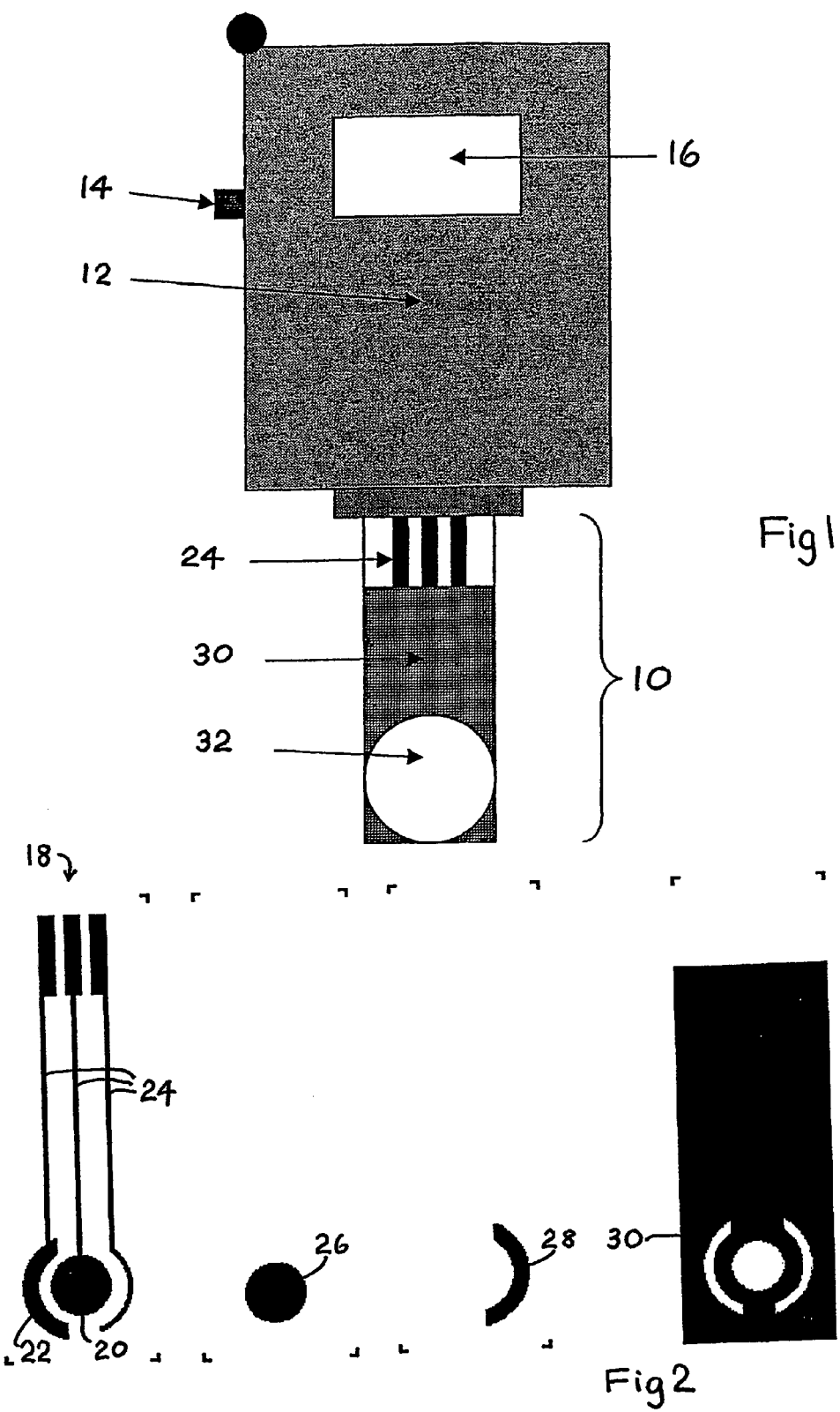

DETECTION OF ALLERGEN-ASSOCIATED MATERIALS

TECHNICAL FIELD

The present invention relates to methods and apparatus for the detection of allergen-associated materials, particularly in an indoor environment. It is especially concerned to facilitate rapid, economical and simple detection which is suitable for domestic use.

The incidence of allergic reactions to materials commonly encountered within the home environment is ever increasing. Common allergens include cat dander, dust mite faeces, cockroach detritus and the mould *Aspergillus niger*. A primary reason for this increase in allergies has been attributed to changes in lifestyle as a result of improved living standards. Many homes in the developed world are carpeted and contain many soft furnishings as well as being centrally heated and double-glazed. All of these factors summate to produce a warm and moist environment for propagation of allergens whilst at the same time preventing their 'natural' removal.

Given the dramatic increase in the number of people suffering from allergies, there is a need for tools to help sufferers manage their lifestyle appropriately. Simple diagnostic tests could be used at home to help to assess the levels of allergens or allergen-containing materials present. This would allow the sufferer to perform routine environmental control procedures as required. Soft furnishings, such as mattresses, duvets, pillows, armchairs and other items such as carpets and curtains are well-known to act as repositories of allergen-containing materials. By routinely assessing their allergen levels, appropriate cleaning or replacement regimes may be implemented and maintained.

DISCLOSURE OF INVENTION

The present invention is based on the discovery that commonly occurring allergen-associated materials are highly redox-active. Thus they can be oxidised at an electrode. Hence measurement of the redox activity of a sample of material (e.g. household dust) can be used to indicate the presence of allergen-associated materials, and possibly to give some quantitative information.

Thus in one aspect the invention provides a method of testing an indoor environment for the presence of allergen-associated materials comprising (a) collecting a sample of dust from the indoor environment; and (b) measuring the redox activity of the sample, thereby providing data indicative of the presence of allergen-associated material.

Redox activity can be measured in various ways, as is well known. For example, the optical properties of some dyes can be used to provide a quick indication of levels of redox activity suggestive of significant levels of allergen associated materials. However we have concentrated on electrochemical techniques, e.g. amperometry, voltammetry, coulometry and related electrochemical techniques.

BRIEF DESCRIPTION OF DRAWINGS

FIG. 1 is a view of a sensor device embodying the invention.

FIG. 2 is a schematic diagram for use in explaining the construction of the electrode assembly of the device shown in FIG. 1.

MODES FOR CARRYING OUT THE INVENTION

Figure 3:
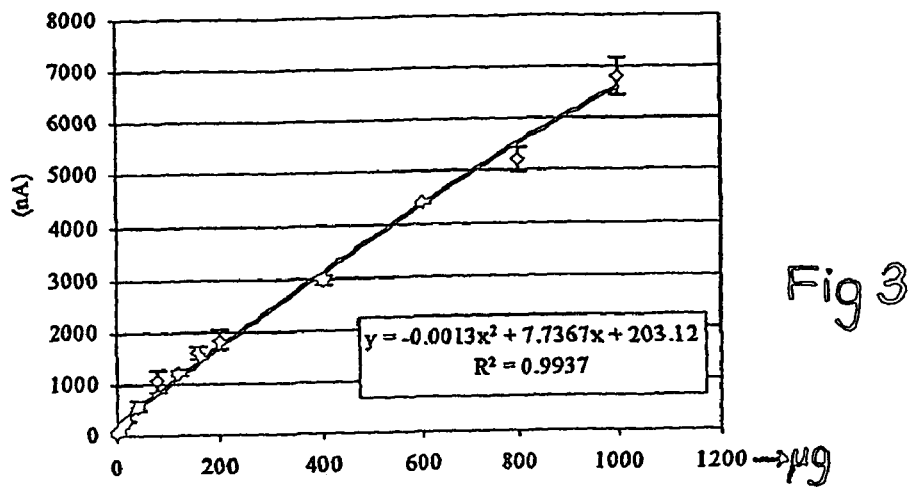
FIGS. 3-5 are graphs showing the response of the device to cockroach detritus, dust mite faeces and household dust, respectively.

FIG. 1 shows a sensor device consisting of a disposable electrode assembly 10 releasably connection to a prototype hand-held meter 12 constructed to our specifications by Cranfield Impact Centre (Cranfield, UK). The design employs a single chip microcomputer incorporating low power electronic circuitry. The meter is ruggedly constructed from surface mount components and is housed within a calculator-sized case. The meter case is designed to allow the electrode assembly 10 to be plugged in directly without an interconnecting cable. The meter has been designed on the basis of a future production model. The potential difference between the working and reference electrodes of the assembly 10 (see below) is adjustable.

A measurement sequence is initiated by pressing a button 14 with automatic termination after a predetermined time, e.g. 7 min. The threshold current setting and bias voltage can be manually adjusted using a screwdriver via two internally mounted trimmers with the aid of a voltmeter. An eight character alphanumeric LCD 16 displays the meter output in the form of the working electrode current in nanoamps. At the end of the assay process, the meter calculates and displays the mean working electrode current over a set period, e.g. the last 3 minutes of the measurement process. Power is supplied by a removable UK standard 9 Volt battery with a lifetime of >200 measurements.

The electrode assembly 10 was produced by screen printing onto 250 µm thick polyester sheet, using the patterns shown in FIG. 2.

Three-electrode devices were mass-manufactured in house by a multi-stage screen-printing process using a DEK 248 machine (DEK, Weymouth, UK) and screens with appropriate stencil designs (60 per screen) fabricated by DEK Precision Screen Division. The stainless steel screen mesh (77 wires $cm^{-1}$) was mounted at 45° to the print stroke. Emulsion thickness was 13 µm and 18 µm for the solvent and water-resistant screens respectively.

The first printing step produced the pattern 18. This includes a working electrode 20 (circular, with a planar area: 0.16 $cm^2$), counter electrode 22 and basal tracks 24, fabricated from I45R carbon ink (MCA Services Ltd., Cambs., UK). The working electrode was either used without further alteration, or else subsequently overlaid with a screen-printed layer 26 of electrocatalytic material. The general role of electro-catalysts is to oxidise electroactive species selectively and reduce the potential at which the analyte is oxidised relative to other electroactive species in the sample matrix. The electrocatalyst used was MCA 4a (MCA Services Ltd.), a commercially available carbon powder, containing 5% rhodium plus promoters, made into a screen-printable paste by mixing 1:4 in 2% w/v HEC in buffer-electrolyte. Previous work in our laboratories has identified MCA4a as a stable and reproducible means of reducing the operating potential required to oxidise hydrogen peroxide, a product in many enzyme-catalysed reactions.

The reference electrode 28 was printed using ink containing 15% silver chloride in silver paste (MCA Services Ltd.). The basal tracks were insulated from the measurement solution using an epoxy-based protective coating 30 formed from ink 242-SB (Agmet ESL Ltd., Reading, UK). The insulation layer also defined the shape and area of the 3 electrodes exposed to the measurement solution. The electrodes were then cured at 125° C. for 2 h. This heat treatment also served to stabilise the electrocatalytic working electrode pad to allow usage in aqueous solutions.

A 1.1 cm diameter Whatman 114 filter disc 32 (Whatman Ltd., Maidstone, UK) was placed over the 3-electrode assembly so that, when wetted with sample, it completed the electrochemical circuit. A 20 μl sample was deposited onto the filter paper and the working electrode poised at +300 mV versus the Ag/AgCl reference. The system was allowed to equilibrate in the presence of sample, and the current value noted at 1 or 2 min. (laboratory based tests) or 7 min. using the field-based hand-held potentiostat shown in FIG. 1. Tests were performed at ambient temperature. Phosphate buffer, pH 7.8, 0.1 M (Sigma, Poole, UK) containing 0.1 M KCl, prepared with deionised reverse osmosis water (Elgastat system, Elga, High Wycombe, Bucks., UK) was used in all tests.

Figure 4:
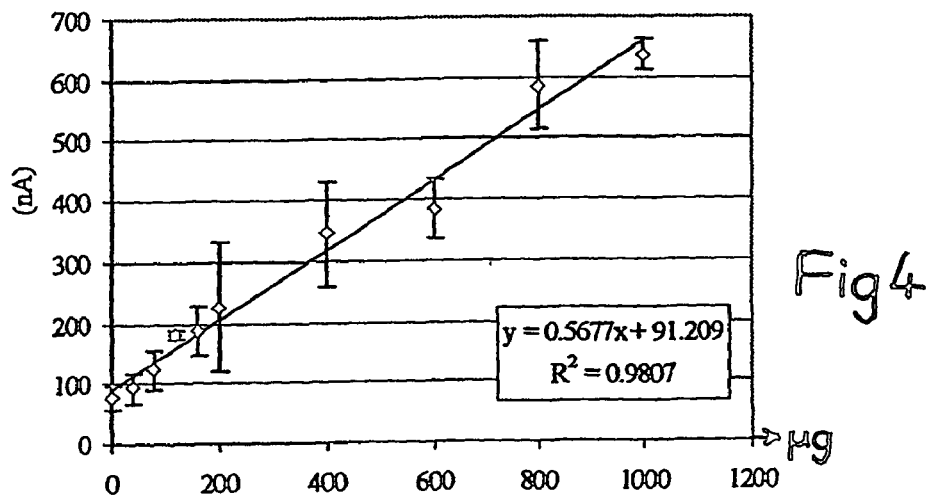
Figure 5:
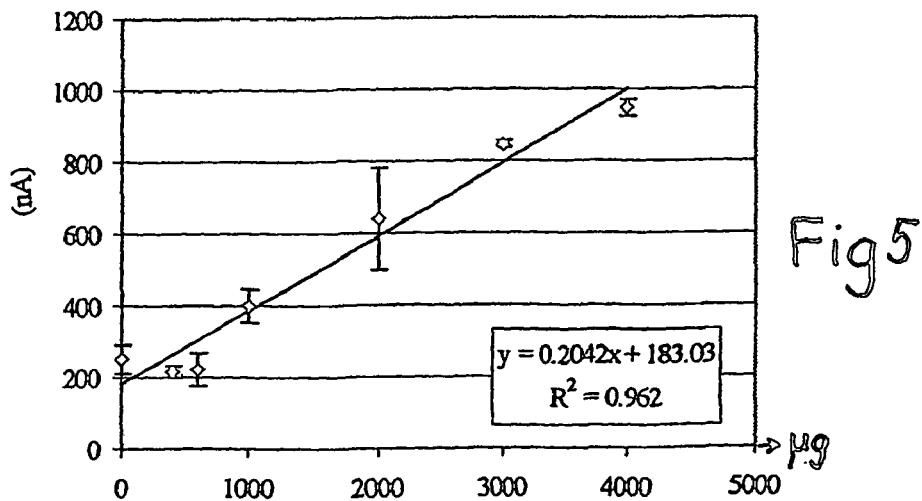

Samples of cockroach detritus were mixed with a buffer salt solution, containing electrolyte. Aliquots thereof were applied directly to the applicator pad. The sensor was poised at a suitable potential and the current response recorded after a set time period. As shown by FIG. 3, increasing amounts of sample material (from 0-1000 μg) resulted in a concomitant increase in device response. Similar trends were observed with dust mite faeces (0-1000 μg) and household dust samples (0-4 mg) as shown in FIGS. 4 and 5.

Further tests used the same electrode assembly 10 but coupled to an autolab Electrochemical Analyser with GPES3 software (Ecochemie, Utrecht, NL). The allergenic samples were as follows.

Dust mite faeces (*Dermatophagoides farinae*) and cockroach detritus were in powder form. The latter material consisted of dried cockroach ground to relatively even consistency by mortar and pestle.

Cat allergen extract was supplied by Bayer and was derived from the precipitate formed when acetone is added to an aqueous extract of cat hair source material (hair clippings and/or shavings). The aqueous extraction fluid consisted of Glycero-Coca's extraction fluid containing 0.5% sodium chloride and 0.275% sodium bicarbonate (by weight) with 50% glycerol (v/v) as preservative. The preparation was labelled as 10 000 BAU (Bioequivalent Allergy Units) mL$^{-1}$, equating to an extract potency of 10-19.9 Fel d I mL$^{-1}$.

The German cockroach extract (*Blattella germanica*) was supplied by Bayer as a 1:10 w/v extract in Glycero-Coca's extracting fluid. No BAU or allergy unit data were provided.

Short ragweed pollen (*Ambrosia elatior*) was from Biopol, labelled as collected under vacuum in Illinois, USA in August 1998, subsequently sieved, washed with acetone to remove fats and trace pesticides before drying at 38° C. for 24 h under vacuum. The batch was found to have <1 ppm heavy metals, 0.18% foreign pollen, 0.74% mould spores, 0.74% plant parts, <1% soil particles and <7% moisture. A potency test revealed the batch to contain 2733.8 U/g antigen E, the most important of the Ragweed pollen allergens.

*Aspergillus niger* (Biopol) was grown on totally synthetic media and collected in April 1998. The sample was ground, washed in acetone and confirmed non-viable and was certified >99% fungi. Cat allergen (Biopol) was labelled as 274.8 Cat I concentration units/g, with no additional data or definition given. The household dust sample was collected by vacuum cleaner from a typical UK detached residence occupied by 2 adults and 1 cat.

The applied working electrode potential was varied between 0 and +800 mV (vs. Ag/AgCl) and the subsequent effect on the sensor response to 5% w/v preparations of cockroach detritus, dust mite faeces and dust samples recorded. Tests were performed on both bare carbon and rhodinised carbon electrodes.

Signal Versus Standard Deviation Ratio

Maximisation of the signal:SD ratio was considered the most important performance criterion with regard to selection of the optimum detection potential. Correspondingly, signal and SD data (8 replicates) was obtained on both working electrode types using 5% w/v cockroach detritus across the potential range 200-800 mV. The data is summarised in Tables 1 and 2.

TABLE 1

Signal and reproducibility data (n = 8) for 5% w/v cockroach detritus in buffer on bare and rhodinised carbon electrodes poised at different potentials. Amperometric responses were recorded after 1 and 2 min.

| Material | Potential (mV) | Mean signal (nA) | | SD (n = 8) | | Signal:SD | |
|---|---|---|---|---|---|---|---|
| | | 2 min | 1 min | 2 min | 1 min | 2 min | 1 min |
| Bare carbon | 200 | 217 | 316 | 31.7 | 36.5 | 8.5 | 8.7 |
| | 350 | 1007 | 1198 | 76.3 | 104.7 | 13.2 | 11.4 |
| | 500 | 1866 | 2420 | 77.4 | 111.1 | 24.1 | 21.8 |
| | 700 | 3371 | 4575 | 70.0 | 133.6 | 48.2 | 33.9 |
| | 800 | 4000 | 5472 | 371.8 | 395.0 | 10.8 | 13.9 |
| Rhodinised carbon | 200 | 2165 | 2496 | 279.1 | 296.3 | 7.8 | 8.4 |
| | 350 | 4286 | 6773 | 389.8 | 392.7 | 11.0 | 17.3 |
| | 500 | 5763 | 8689 | 411.3 | 397 | 14.0 | 21.9 |
| | 700 | 944 | 1258 | 98.3 | 138 | 9.6 | 9.1 |
| | 800 | — | — | — | — | — | — |

TABLE 2

Signal and reproducibility (n = 8) data for 5% w/v dust mite faeces in buffer and 5% household dust in buffer on bare carbon electrodes poised at different potentials. Readings recorded after 1 and 2 min.

| Sample | Potential (mV) | Mean signal (nA) | | SD (n = 8) | | Signal:SD | |
|---|---|---|---|---|---|---|---|
| | | 2 min | 1 min | 2 min | 1 min | 2 min | 1 min |
| Dust mite faeces on bare carbon | 350 | 348 | 448 | 30.3 | 44.4 | 11.5 | 10.1 |
| | 500 | 1015 | 1266 | 76.9 | 98.6 | 13.2 | 12.9 |
| | 700 | 1996 | 2501 | 185.2 | 211.8 | 10.8 | 11.8 |
| | 800 | 3354 | 3911 | 271.5 | 354.3 | 12.4 | 11.0 |
| Household dust on bare carbon | 350 | 125 | 153 | 7.9 | 10.0 | 15.9 | 15.3 |
| | 500 | 258 | 325 | 25.0 | 26.3 | 10.3 | 12.4 |
| | 700 | 561 | 718 | 74.9 | 87.4 | 7.5 | 8.2 |
| | 800 | 744 | 1000 | 70.0 | 94.6 | 10.6 | 10.6 |

Calibration Data

Calibration data relating to the 8 allergen-containing materials tested are given in Table 3. Buffer-electrolyte solutions were used for the zero analyte control solutions except for the cat allergen extract, which contained the same amount of glycerol (25%) as present in the most concentrated allergen-containing sample.

TABLE 3

Calibration and analytical performance data for the chosen allergen containing materials. Tests were performed on bare carbon electrodes poised at +700 mV (vs. Ag/AgCl) and the amperometric response, in nA, recorded after 1 and/or 2 min. y = response (nA); x = concentration (% w/v); n = 5.

| Sample | Analysis time (min) | Conc. range (% w/v) | Equation | Correlation coefficient ($R^2$) | Limit of detection (% w/v)[a] | % CV[b] |
|---|---|---|---|---|---|---|
| Cockroach detritus | 2 | 0-1 | y = 2020.62x + 48.5 | 0.9979 | 0.0029 | 3.2-16 |
| | | 0-5 | y = −245.6$x^2$ + 2467.90x − 11.4 | 0.9989 | | |
| Dust mite faeces | 2 | 0-0.05 | y = 3286.5x + 34.0 | 0.9988 | 0.0018 | 0.9-12 |
| | | 0-5 | y = 191.97 Ln(x) + 762.4 | 0.9608 | | |
| Household dust | 2 | 0-5 | y = 142.88x + 58.2 | 0.9956 | 0.0420 | 4.0-15 |
| | | 0-20 | y = 132.82x + 63.9 | 0.9590 | | |
| German cockroach extract | 1 | 0-20 | y = 449.15x + 40.1 | 0.9957 | 0.0134 | 4.6-19 |
| | 2[c] | | y = 12.57$x^2$ + 96.59x + 119.1 | 0.9988 | | |
| Cat allergen extract | 1 | 0-50 | y = 8.98x + 46.9 | 0.9911 | 1.0356 | 4.2-16 |
| | 2 | | y = 4.12x + 32.2 | 0.9619 | | |
| Ragweed pollen | 1 | 0-4 | y = 2058.62x + 317.7 | 0.9932 | 0.0291 | 1.9-12 |
| | | 0-10 | y = −134.21$x^2$ + 2456.53x + 288.7 | 0.9944 | | |
| | 2 | 0-4 | y = 1291.79x + 129.3 | 0.9974 | | |
| | | 0-10 | y = −32.134$x^2$ + 1348.14x + 151.0 | 0.9971 | | |
| Cat allergen | 1 | 0-10 | y = 512.11x + 145.2 | 0.9957 | 0.0879 | 3.7-12 |
| | | | y = −7.86$x^2$ + 584.32x + 103.3 | 0.9972 | | |
| | 2 | | y = 401.51x + 22.4 | 0.9820 | | |
| | | | y = 20.89$x^2$ + 209.52x + 88.9 | 0.9986 | | |
| *Aspergillus niger* | 1[d] | 0-10 | y = −21.39$x^2$ + 404.56x + 176.1 | 0.9799 | — | 0.8-26 |
| | 2[d] | | y = −13.61$x^2$ + 299.95x + 101.1 | 0.9877 | | |

[a]Limit of detection: based on 3 × SD of zero analyte response
[b]% CV (% coefficient of variation) = [SD/mean response] × 100%
[c]No linear data at 2 min.
[d]No linear data at 1 or 2 min.

Optimum Measurement Potential

All sample types yielded amperometric responses across the potential range tested, with µA currents being recorded at higher potentials for both electrode materials. At a potential of +700 mV on a rhodinised carbon surface, 5% w/v cockroach detritus yielded a response value of >10 µA. Higher response values were always obtained for rhodinised carbon electrodes compared with bare carbon electrodes at comparable potentials (~3× at a potential of +600 mV). However, the baseline values were also correspondingly higher, resulting in a lower Signal:baseline ratio for the rhodinised carbon. Whilst increases in signal size were observed for both materials with increasing potential, over-high potentials are not advisable for 3 reasons: (i) steep increases in baseline levels, (ii) unreliability of the screen-printed reference electrodes at excessive working electrode potentials, (iii) electrolysis of the supporting medium.

Signal Versus Standard Deviation Ratio

Although the data in Tables 1 and 2 indicate that rhodinised carbon provided a more reactive surface for oxidation of cockroach detritus, this was at the expense of reproducibility. The bare carbon material gave SD values that were generally well below 10% of the signal value, compared with rhodinised carbon where more than half of the 72 tests performed yielded SD values of >10% of the signal response.

The signal:SD ratio showed that overall, bare carbon is better than rhodinised carbon (column 5, Table 1). This is because the ratio was higher for bare carbon across the whole range of potentials tested, reaching a value of 48.2 at a potential of +700 mV (c.f. 9.6 for the electrocatalyst). Bare carbon working electrodes were correspondingly further examined with 5% w/v dust mite faeces and household dust, with results being summarised in Table 2. Similar trends to those recorded for cockroach detritus were observed (high mean signal values and SD values generally <10% of mean signal responses).

A comparison of the signal:SD ratio on bare carbon for the 3 allergens tested indicates that a detection potential of +700 mV is optimum for the measurement of cockroach detritus, whilst the signal:SD ratio for dust mite faeces and household dust is relatively constant across the potential range tested. Correspondingly, a potential of +700 mV was chosen for further examination, based on the preferential cockroach detritus result. Further examination of the data indicates that there is little change in test performance when increasing the measurement time from 1 to 2 min. A 1 min test would be more attractive to end-users of the device and was therefore used in subsequent studies.

Calibration Data

Table 3 indicates that there is a relationship between sample concentration (also quantity, since the same sample volume was applied in all tests) and test response for all of the 8 allergen-containing materials. For *Aspergillus niger*, no linear response was apparent across the concentration range tested, although it was clearly possible to distinguish between samples containing 0 and 0.02% w/v of this allergen-containing material.

The order of electroactivity for the 8 allergen-containing materials tested under the applied experimental conditions was (from most to least electroactive): BIOPOL Ragweed pollen and cockroach detritus; BIOPOL *Aspergillus niger*, BIOPOL Cat Allergen; BAYER German cockroach extract and Dust mite faeces; household dust; BAYER Cat Allergen. However, the BAYER samples were supplied as solution extracts and not solid materials, thus their true position in the electroactivity series may be different Furthermore the extracts contained glycerol, which although not electroactive, may act to partially block the membrane and interfere with the sample oxidation process leading to a reduction in signal response, particularly at high sample concentrations.

The BAYER Cat allergen sample contained between 10-19.9 Fel d I units per ml. The device is therefore capable of detecting samples containing as little as 0.02-0.04 Fel d I units. The absence of glycerol in the measurement solution would be expected to improve the detection limit.

Limits of detection vary according to the particular allergen-containing material tested, but in the case of the 3 BIOPOL samples (Ragweed pollen, cat allergen and *Aspergillus niger*) and also cockroach detritus, it was possible to distinguish between samples containing 0.0018% w/v sample (0.36 µg material per test) and allergen-free controls.

Table 3 shows that test reproducibility, expressed as coefficients of variation (100%×SD/mean response) are generally under 12% although, in one case, a value of over 20% was recorded. Testing of the electrodes with hydrogen peroxide, a homogeneous highly electroactive solution, consistently yields CV values of around 4%, indicating that the main cause of irreproducibility is sample non-homogeneity.

Sensor Selectivity

The electrochemical approach, by not employing an analyte-selective step (such as an appropriate analyte extraction or ligand binding procedure) is non-specific and it must be considered that some materials of a non-allergenic nature may also exhibit electroactivity. Thus any assay based on direct electrochemistry without some form of selective analyte extraction or recognition will be prone to interference. Potential electroactive interferents in the home will include organic acids (ascorbic, tannic, glutamic, malic, citric etc.), proteins and sugars from food-based residues and certain cleaning/sterilising products.

Methods to improve test selectivity, such as sample preparation and the use of affinity binding agents were considered. However, two problems arise: (1) increased assay complexity, which is highly undesirable in a home-use test, and (2) the need for a specific sensor to measure each individual target compound. The ethos of our approach has been to create a very simple screening tool primarily for monitoring purposes. The essential point with this non-specific system is that the devices are employed appropriately, that is, by measuring in regions where allergens would be expected to accumulate (under beds, on curtains, in pillows and mattresses), rather than in places where non-allergens will tend to accumulate (food preparation and consumption areas). In this manner, a degree of semi-selectivity is achieved. Essential to the strategy would be a monitoring regime, in which the user assesses test sites on a routine basis, so that any sharp increases in levels of electroactive materials may be rapidly identified.

Airborne Allergen Monitoring

Many allergens originate as, or may become, airborne during their lifecycle. Indeed, it is the inhalation of airborne allergens that is the initiator of a great number of allergic responses. Nevertheless, the detection of allergens on surfaces (curtains, bedding) and within soft furnishing (mattresses, pillows) is directly linked to airborne allergen levels as well as identifying the allergen source. In the case of airborne allergens such as pollens, a particle trap, with subsequent electrochemical detection would provide a valid approach.

Device Deployment Scenarios

Four potential device deployment scenarios are described below. It is intended with all of these scenarios that the end-user obtains information to aid decision making processes, such as replacement of pillows, cover/replacement of mattresses, washing of curtains, further cleaning etc.). The sensor will provide an overall assessment, and not an indication of how many different allergens are present or their identity. The electrodes would be used in conjunction with a meter for provision of quantitative or semi-quantitative data as required. These devices are inexpensive, as proven by the practice of the blood glucose biosensor manufacturers who distribute meters at no cost to the end-user, whilst profiting on the sale of disposable screen-printed electrodes.

Scenario 1: 'Lifestyle' Diagnostics

There is a growing interest in diagnostic tools that can be deployed in conjunction with tasks that are routinely performed as part of an individuals general lifestyle. An example is vacuum cleaning. Application of a compact filter device to a small portion of the vacuum cleaner suction inlet would provide a means of sample collection without the need for additional input from the consumer. The contents of the filter would be recovered by a simple wash, and the electroactivity of the resultant solution measured.

Scenario 2: Discrete Sampling

In certain cases it may be more appropriate to assess electroactive compounds at particular sites, such as curtains or under beds. A small, dedicated sampling device could serve to trap loosely adhered material to a filter. Recovery and dissolution of the trapped components would follow coupled to subsequent electrochemical evaluation.

Scenario 3: Airborne Contaminants

The development of a sensor to measure airborne allergens would provide a powerful tool to allergy sufferers. Again a suction device, linked to a liquid (buffer-electrolyte) trap and electrochemical interrogation could be activated at specific time intervals to provide information on airborne allergen levels in the atmosphere. Appropriate liquid handling could be used to replace spent solutions with fresh liquid, coupled to self-cleaning potential-time waveforms to minimise electrode-fouling problems. This portable device would be appropriately sited near ventilation sources to alert the user to elevations in levels of airborne materials, including pollens, and thus allow appropriate steps to be taken (close windows, eye protection, medication).

Scenario 4: Specific Identification

A recognised drawback of the electrochemical procedure is non-specificity. An alternative use of the technology would be to identify electroactive hot-spots, from which samples would be collected and posted to a centralised laboratory for specific identification, such as by high-throughput immunoassay. End-users could then be informed of the specific allergen(s) present and, after consideration of the collection location, be provided with information on how best to reduce allergen contamination.

Electrode assemblies as described with reference to FIGS. 1 and 2 can be mass produced very cheaply to provide disposable units. They may be packed individually in barrier materials, e.g. foil pouches. The filter paper pad may have been impregnated with solutes for producing an electrolyte/buffer solution. Thus a typical mode of use of the apparatus would be:

1. remove sensor electrode assembly from foil pouch.
2. wipe surface with sensor to collect a sample on the filter paper attached to the sensor.
3. apply a few drops of (tap) water to the sensor i.e. drop the water onto the filter paper.
4. insert the sensor into the hand-held device and switch the instrument on.
5. wait (a few) minutes then read the result.

A more sophisticated device could be aimed at the specific detection of allergenic material. The use of an immobilised antibody matrix, coupled to a dedicated air displacement pump, would allow specific sampling to be carried out. The antibodies will only trap the desired target e.g. dust mite faeces etc. Detection and quantification of the target analyte will be carried out, based on our discovery of redox activity, using either electrochemical (as shown with the hand-held meter in the Figure) or optical measurements.

To demonstrate the simple use of optical measurements we conducted a series of experiments with dust samples collected from the home environment. We prepared aqueous preparations of these samples to which we added two different dye reagents, ferrocyanide and 2,2'-azino-di-[3-ethylbenziazoline-6-sulfonate]. For a number of these samples we observed a significant colour change. Of course this could be made quantitative using colourimetric techniques, and other redox dyes could be used.

The invention claimed is:

1. A method for detecting the presence of a redox-active allergen-associated material, comprising:
   (a) obtaining a sample of dust containing a redox-active allergen associated material; and
   (b) measuring the redox activity of the sample in an electrochemical device that comprises:
      an electrode assembly,
      an absorbent pad overlying the electrode assembly, and
      an electrolyte solution in contact with both the electrode assembly and the absorbent pad after having applied said sample to said absorbent pad,
      wherein the measurement of redox activity of the allergen-associated material relates directly to the presence of said allergen-associated material in the sample;
      thereby providing data indicative of the presence of the allergen-associated material;
      wherein said method does not employ ligand-binding.

2. The method according to claim 1, wherein said step (a) comprises wiping a surface in an indoor environment.

3. The method according to claim 1, wherein said step (a) comprises drawing a stream of air from an indoor environment through a filter so that dust is collected on the filter.

4. The method according to claim 1, wherein said step (b) employs an electrochemical measurement of redox activity.

5. The method according to claim 4, wherein said electrochemical measurement employs a technique selected from the group consisting of amperometry, voltammetry and coulometry.

6. The method according to claim 5, wherein said electrode assembly is disposable.

7. The method according to claim 4, wherein said electrode assembly is disposable.

8. The method according to claim 7, further comprising a preliminary step of preparing the electrode assembly by screen printing the electrode assembly onto an insulating substrate using a conductive ink.

9. The method according to claim 8, wherein said screen printing comprises (a) printing a working electrode and optionally a counter-electrode with a carbon ink; and (b) printing a reference electrode with a silver chloride and silver paste.

10. The method according to claim 1, wherein the pad initially contains dry solutes which are converted by the addition of water into the electrolyte solution.

11. The method according to claim 10, wherein the electrolyte solution is a buffer.

12. The method according to claim 10, wherein the dust sample is collected by wiping a surface in the indoor environment with the absorbent pad which is overlying the electrode assembly.

13. The method according to claim 1, wherein the electrolyte solution is a buffer.

14. The method according to claim 13, wherein the dust sample is collected by wiping a surface in the indoor environment with the absorbent pad which is overlying the electrode assembly.

15. The method according to claim 1, wherein the dust sample is collected by wiping a surface in the indoor environment with the absorbent pad which is overlying the electrode assembly.

16. The method of claim 1, wherein said allergen-associated material comprises cat dander.

17. The method of claim 1, wherein said allergen-associated material comprises or is prepared from dust mite faeces or cockroach detritus, or both.

18. The method of claim 1, wherein said allergen-associated material comprises *Aspergillus niger*.

19. The method of claim 1, wherein said allergen-associated material comprises pollen.

20. The method of claim 1, which does not employ analyte extraction or other analyte-specific steps.

21. The method of claim 1, wherein said dust sample is household dust.

22. The method of claim 1, wherein said dust sample is obtained from a soft furnishing, mattress, duvet, pillow, armchair, carpet or from a vacuum cleaner.

23. A method of testing en indoor environment for the presence of a redox-active allergen-associated material, comprising:
   (a) collecting a sample of dust from the indoor environment containing a redox-active allergen associated material; and
   (b) measuring the redox activity of the sample in an electrochemical device that comprises:
      an electrode assembly,
      an absorbent pad overlying the electrode assembly, and
      an electrolyte solution in contact with both the electrode assembly and the absorbent pad after having applied said dust sample to said absorbent pad,
      wherein the measurement of redox activity of the allergen-associated material relates directly to the presence of said allergen-associated material in the sample;
      thereby providing data indicative of the presence of the allergen-associated material;
      wherein said method does not employ ligand-binding.

* * * * *